(12) United States Patent
Bernard

(10) Patent No.: US 6,633,775 B1
(45) Date of Patent: Oct. 14, 2003

(54) SYSTEM FOR SYNCHRONIZING ACTIVATION OF AN IMAGING DEVICE WITH PATIENT RESPIRATION

(75) Inventor: Philip A. Bernard, Golden, CO (US)

(73) Assignee: The UAB Research Foundation, Birmingham, AL (US)

( * ) Notice: Subject to any disclaimer, the term of this patent is extended or adjusted under 35 U.S.C. 154(b) by 0 days.

(21) Appl. No.: 09/623,156

(22) PCT Filed: Feb. 22, 1999

(86) PCT No.: PCT/US99/03806

§ 371 (c)(1),
(2), (4) Date: Oct. 16, 2000

(87) PCT Pub. No.: WO99/43254

PCT Pub. Date: Sep. 2, 1999

Related U.S. Application Data

(60) Provisional application No. 60/076,371, filed on Feb. 27, 1998.

(51) Int. Cl.[7] .............................. A61B 5/00; H01G 1/38
(52) U.S. Cl. .......................................... 600/428; 378/95
(58) Field of Search ................................. 600/413, 407, 600/428, 529, 532, 534, 537; 378/95

(56) References Cited

U.S. PATENT DOCUMENTS

| | | | | | |
|---|---|---|---|---|---|
| 4,387,722 A | * | 6/1983 | Kearns | .................... | 600/529 |
| 4,712,560 A | * | 12/1987 | Schaefer et al. | ............ | 600/413 |
| 4,763,075 A | * | 8/1988 | Weigert | ...................... | 324/318 |
| 5,271,055 A | * | 12/1993 | Hsieh et al. | ................. | 378/95 |
| 5,485,850 A | * | 1/1996 | Dietz | ......................... | 600/529 |
| 5,577,502 A | * | 11/1996 | Darrow et al. | ............. | 600/426 |
| 6,298,260 B1 | * | 10/2001 | Sontag et al. | ............... | 600/413 |

* cited by examiner

*Primary Examiner*—Shawna J Shaw
(74) *Attorney, Agent, or Firm*—Gifford, Krass, Groh, Sprinkle, Anderson & Citkowski, P.C.

(57) ABSTRACT

A system is disclosed for synchronizing the activation of an imaging device, such as an X-ray machine, with patient respiration. The imaging device includes a conventional trigger signal input for activating the imaging device in response to a preset signal. The system includes a respirator device, such as a ventilator or respiration band, which provides an output signal indicative of the degree of patient inspiration. A processing circuit is responsive to the output signal from the respiration device and generates the preset signal at a preselected degree of patient inspiration. The output signal from the processing circuit is coupled to the imaging device signal input to activate the imaging means at the preselected degree of patient inspiration.

14 Claims, 3 Drawing Sheets

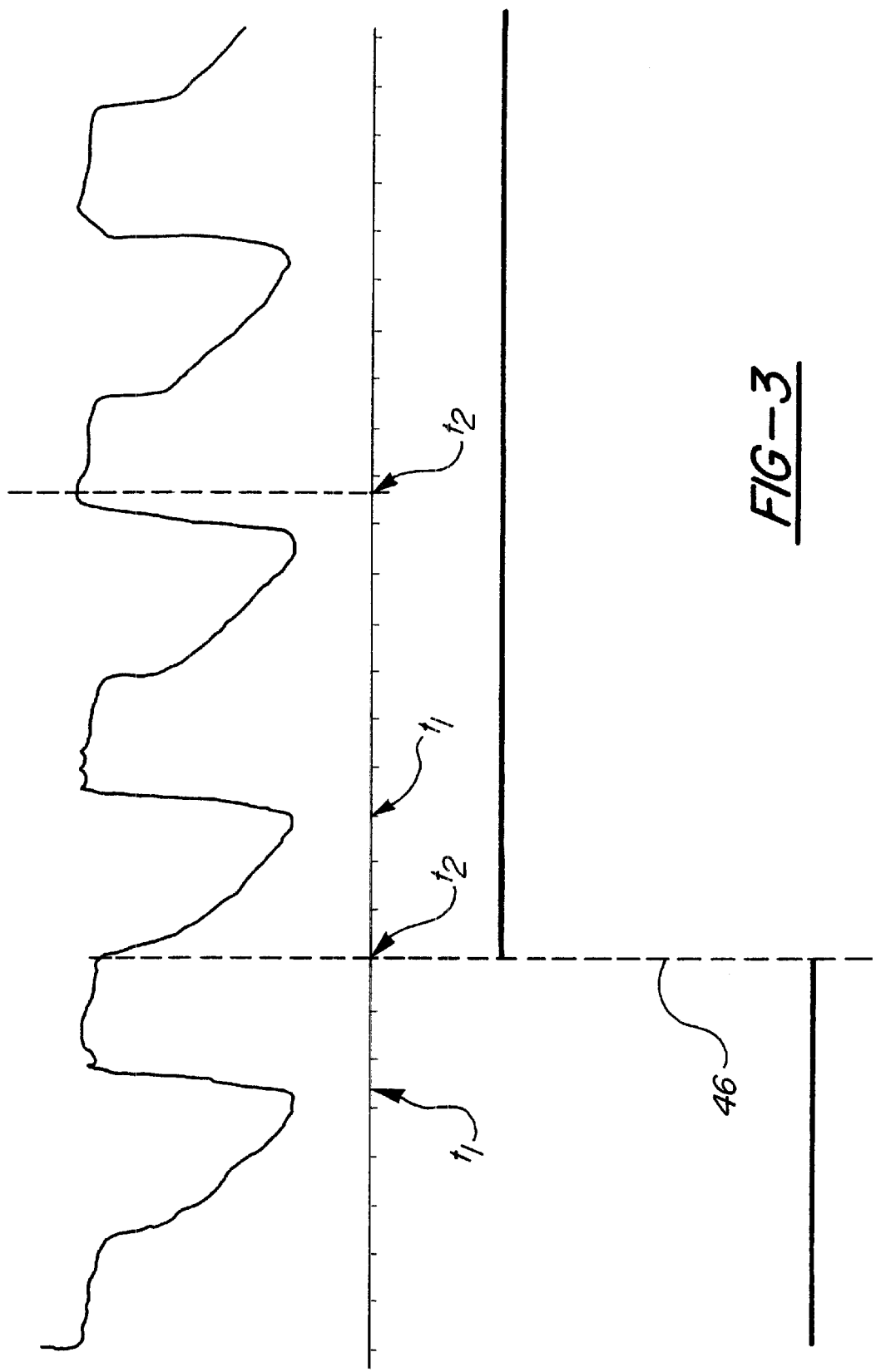

SYSTEM FOR SYNCHRONIZING ACTIVATION OF AN IMAGING DEVICE WITH PATIENT RESPIRATION

This application claims the benefit of Provisional Application No. 60/076,371, file Feb. 27, 1998.

BACKGROUND OF THE INVENTION

I. Field of the Invention

The present invention relates generally to medical devices and, more particularly, to a medical device to synchronize the activation of an imaging device, such as an X-ray machine, with the degree of patient inspiration.

II. Description of the Prior Art

In the operation of medical imaging devices, such as X-ray machines, it is highly desirable to obtain the image at a predefined degree of patient inspiration, at least where an image of the patient's chest area is desired or upper airway films. In many cases, the image is desired at the full or maximum patient inhalation. However, in other cases, the image may be desired at complete exhalation or at some predefined point between complete exhalation and complete inhalation.

In many cases, the patient is merely instructed to either inhale or exhale to the desired degree of inspiration and then maintain that inhalation or exhalation while the image is taken. In other cases, however, the patient is either nonresponsive to commands either through illness or injury or because of the young age of the patient.

In this latter case, it has been the previous practice for the technician operating the imaging equipment to attempt to activate the imaging device at the desired degree of patient inspiration. This, however, has proven extremely difficult to accomplish, especially in the case of an infant patient due to the very high respiration rate of the infant. Consequently, when attempting to obtain an image from an infant at a predetermined degree of inspiration, for example maximum inhalation, it has been previously necessary to obtain multiple exposures from the imaging device of the infant in the hope that one of the multiple images will be either at or near the desired degree of inspiration.

The multiple exposure of patients and particularly infants to imaging devices such as X-ray machines is disadvantageous for two reasons. First, the use of multiple exposures to the X-ray machine in an attempt to obtain one good X-ray image is expensive not only in wasted X-ray film, but also technician time. Secondly, the exposure of the infant to multiple X-ray images necessarily increases the risk to the infant patient of cellular damage from the X-ray exposure.

SUMMARY OF THE PRESENT INVENTION

The present invention provides a system which overcomes all of the above-mentioned disadvantages of the previously known devices.

In brief, the system of the present invention synchronizes the activation of an imaging device, such as an X-ray machine, with the patient's respiration. The imaging device includes a trigger signal input for activating the imaging device in response to a preset signal. Such trigger signal inputs, furthermore, are conventional for imaging devices, such as X-ray machines.

The system of the present invention is used in conjunction with a respiration device which provides an output signal indicative of the degree of patient inspiration. Such a respiration device can comprise, for example, a ventilator or respirator band. In the case of a ventilator, ventilators conventionally provide a direct output signal indicative of the degree of patient inspiration. In the case of a respirator band, the respirator band conventionally includes control circuitry which likewise provides an output signal indicative of the degree of patient inspiration.

A control circuit means is then responsive to the output signal from the respiration device for generating the preset signal at a preselected degree of patient inspiration. The preset signal from the generating means is then connected to the trigger signal input of the imaging device in order to activate the imaging device. Preferably, the control circuit is both solid state based and electrically isolated from the patient.

In practice, the output signal from the respiration device is typically an analog signal. Assuming that the activation of the imaging device is desired at maximum patient inhalation, the control circuit generates the preset signal at maximum inhalation. The preset signal is, in turn, coupled to the trigger input of the imaging device in order to activate the imaging device.

BRIEF DESCRIPTION OF THE DRAWING

A better understanding of the present invention will be had upon reference to the following detailed description when read in conjunction with the accompanying drawing, wherein like reference characters refer to like parts throughout the several views, and in which:

FIG. 3 is a graph illustrating the operation of the present invention.

DETAILED DESCRIPTION OF A PREFERRED EMBODIMENT OF THE PRESENT INVENTION

Figure 1:
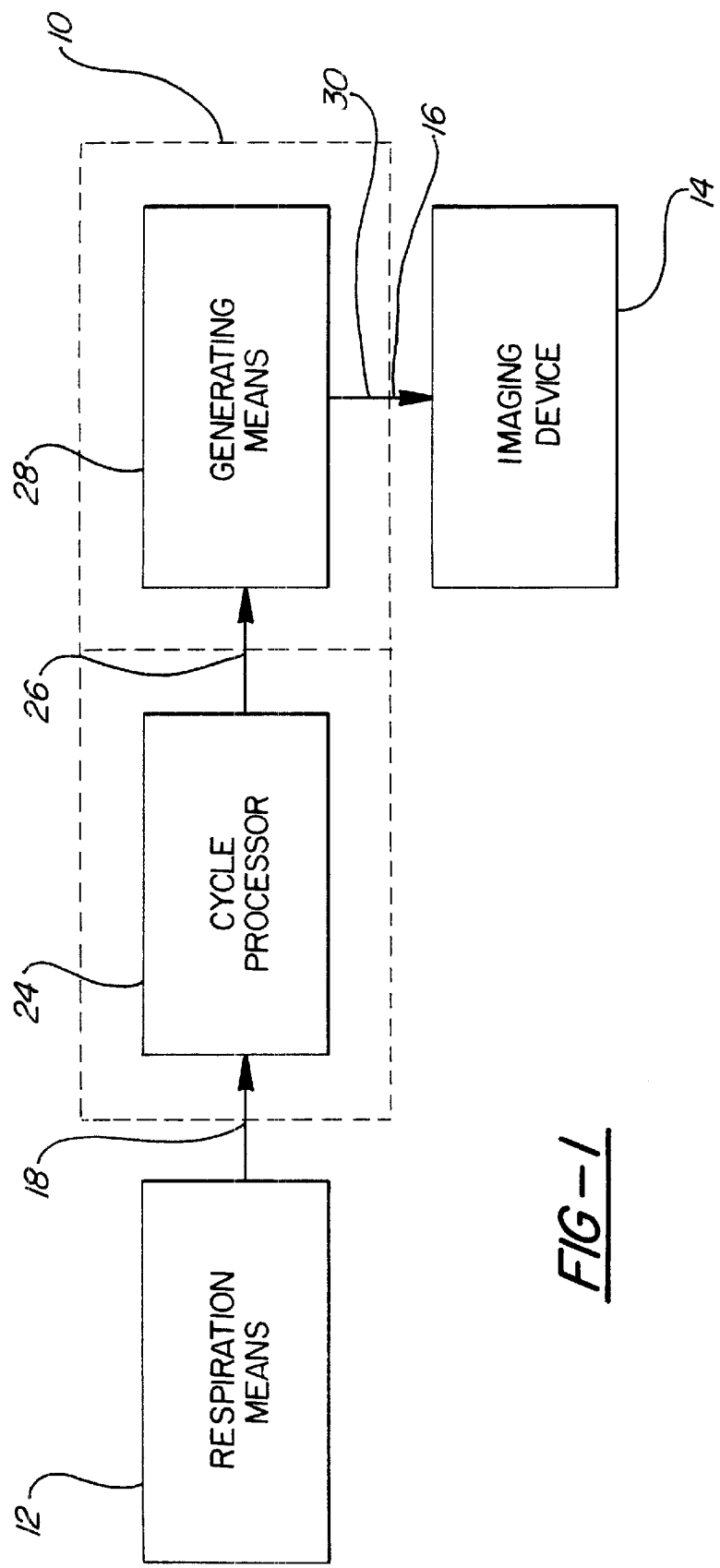
FIG. 1 is a block diagrammatic view illustrating a preferred embodiment of the present invention.

With reference first to FIG. 1, a block diagrammatic view of the synchronization device 10 is there shown for use in conjunction with both a respiration device 12 and an imaging device 14. The imaging device 14 can comprise, for example, an X-ray machine. As such, the imaging device includes a trigger signal input 16 responsive to a preset signal for activating the imaging device 14 and taking the image. For example, the preset signal could comprise a DC voltage of a preset magnitude, such as 5 volts or 24 volts.

Similarly, the respiration device 12 provides an output signal on its output line 18 indicative of the degree of patient respiration. One such respiration signal is shown at 20 in FIG. 3 for exemplary purposes only. As shown in FIG. 3, the respiration cycle includes inhalation beginning at time $t_1$ to maximum inspiration at time $t_2$ followed by patient exhalation. The signal 20 from the respiration device between times $t_1$ and $t_2$ corresponds to the degree of patient inspiration ranging from 0% at time $t_1$ and 100% at time $t_2$.

The respiration means 12 can comprise, for example, a ventilator or respiratory band. Conventional respirators as well as respiration bands include analog output signals corresponding to the patient inspiration signal 20 (FIG. 3).

Referring again to FIG. 1, the output signal 20 from the respiration means 12 is then coupled as an input signal to a cycle processor 24. The cycle processor 24 generates a signal on it s output line 26 whenever the degree of inspiration reaches a preset degree, such as 100% at maximum inhalation.

The out put signal on line 26 from the cycle processor 24 is coupled as an input signal to a generating means 28. The generating means 28 in response to an output signal from the cycle processor 24 generates the preset trigger signal on its output line 30 to the imaging device at its trigger input 16 necessary to activate the imaging device 14 and obtain the desired image.

Figure 2:
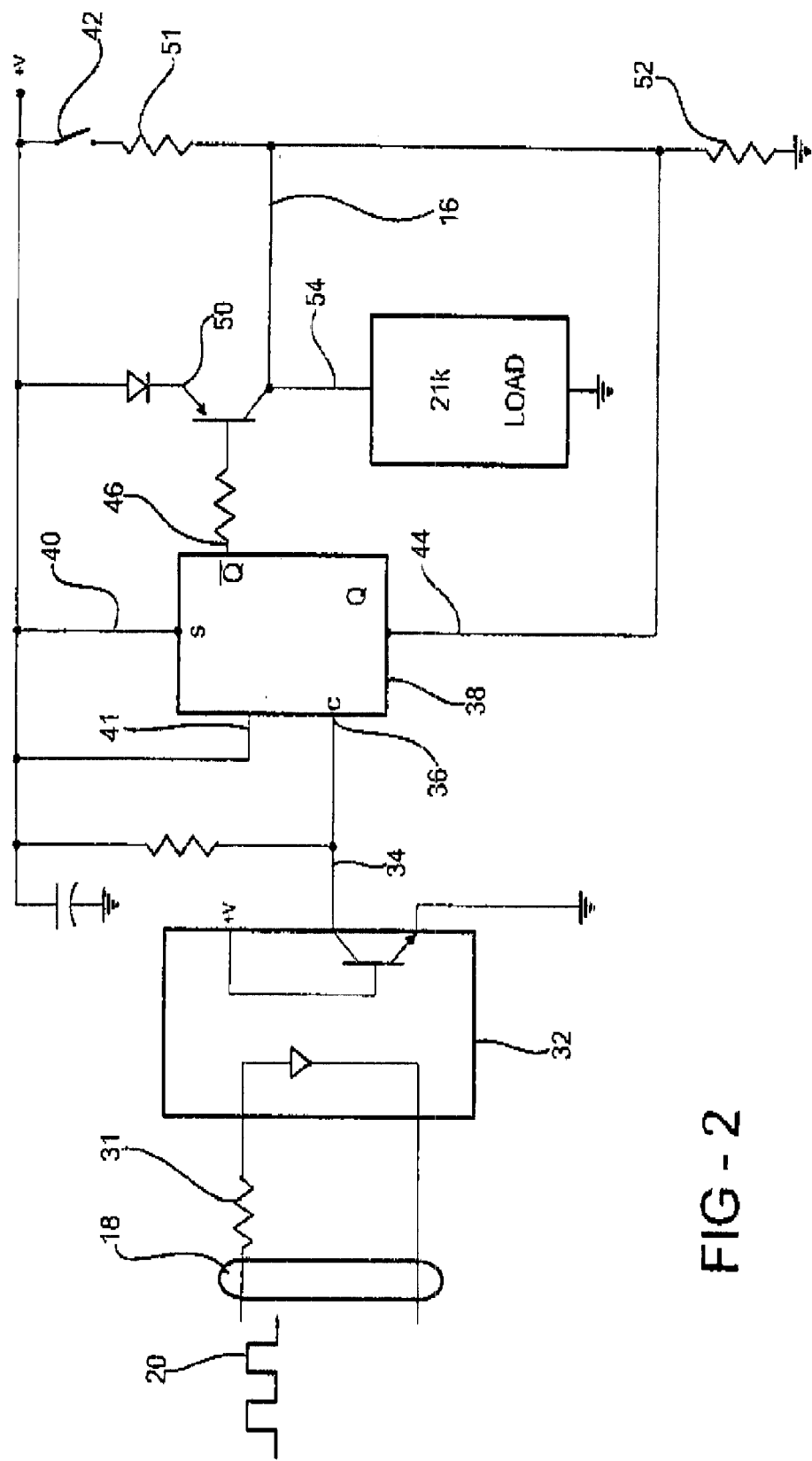
FIG. 2 is a schematic view illustrating the preferred embodiment of the present invention.

With reference now to FIG. 2, there is shown a schematic view of one preferred embodiment of the present invention. In FIG. 2, the output signal 20 from the respiration device 12 is coupled as an input through a resistor 30 to an optoisolator 32. In the well known fashion, the optoisolator 32 generates a signal on its output 34 which corresponds to the inspiration signal 20, but is electrically isolated from the signal 20 and thus from the respirator device 12 on the patient.

The output signal 34 from the optoisolator 32 is coupled as an input signal to the clock input 36 of a D flip-flop 38. A voltage supply V1 holds the $\overline{SET}$ input 40 and data input D 41 of the D flip-flop 38 at a high state while, as long as a switch 42 is maintained in an open position, the $\overline{RESET}$ input 44 of the D flip-flop 38 is maintained at a low state. Consequently, even periodic clock signals on the input 36 to the D flip-flop 38 will not trigger the D flip-flop 38 to switch its $\overline{Q}$ output 46 to a low state as long as the switch 42 is open.

The switch 42, upon closure, is electrically connected to and prepares the imaging device 14 for an exposure. The switch 42 is a conventional input on the imaging device 14.

Upon closure of the switch 42, typically by the medical technician, to prepare the imaging device 14 for an image, current flow through a resistor 51 and resistor 52 causes the $\overline{RESET}$ input 44 of the D flip-flop 38 to go to a high state thus allowing the D flip-flop 38 to be set by the next high input signal on its clock input 36. Consequently, following closure of the switch 42, the D flip-flop 38 is set on the next high input signal on its clock input thus setting its $\overline{Q}$ output 46 to a low state. This in turn renders a transistor 50 conductive. The output 54 from the transistor 50 comprises the preset trigger signal necessary to activate the imaging device 14 and, as such, is coupled to the imaging device trigger input 16. For example, the output signal on the output 54 from the transistor 50 may comprise a preset DC voltage necessary to activate or trigger the imaging device 14.

With reference now to FIG. 3, the actual output signal on the $\overline{Q}$ output 46 from the D flip-flop 38 is there shown as rising from a lower level to a preset upper level at time $t_2$, i.e. the maximum inspiration. Once the D flip-flop 38 has been set, the output 46 will remain in a high state until the switch 42 (FIG. 2) is opened thereby resetting the flip-flop 38.

From the foregoing, it can be seen that the present invention provides a simple and yet effective system for synchronizing the activation of an imaging device, such as an X-ray machine, with a predetermined degree of patient inspiration.

Having described my invention, however, many modifications thereto will become apparent to those skilled in the art to which it pertains without deviation from the spirit of the invention as defined by the scope of the appended claims.

I claim:

1. A system for synchronizing the activation of an imaging device with patient respiration as monitored by a respiratory device, said respiratory device operative to output a respiratory signal indicative of the degree of a patient's respiration during a respiration cycle, said imaging device having a signal input for activating the imaging device in response to a preset signal, said system comprising:

a cycle processor optically coupled to said respiratory device such that said cycle processor is electrically isolated from said respiratory device and generates an electrical output signal that corresponds to said respiratory signal; and a generating device in communication with said cycle processor, said generating device outputting the preset signal to said imaging device in response to the electrical output signal received from said cycle processor.

2. The system as defined in claim 1 wherein said imaging device comprises an X-ray machine.

3. The system as defined in claim 1 wherein said respiratory device comprises a ventilator.

4. The system as defined in claim 1 wherein said respiratory device comprises a respiration detector.

5. The system as defined in claim 1 wherein said respiratory signal comprises maximum inhalation of the patient.

6. The system as defined in claim 1 wherein said generating device comprises a solid state circuit.

7. The system as defined in claim 6 wherein said solid state circuit comprises a flip-flop having an input coupled to said respiratory signal from said respiratory device, said flip-flop having an output signal connected to a switch whereby said output signal causes said switch to change from a first state to a second state, said second state corresponding to said preset signal.

8. The invention as defined in claim 7 wherein said switch comprises a transistor.

9. The system of claim 1 wherein said cycle processor is optically coupled external to said respiratory device.

10. A system for synchronizing the activation of an imaging device with patient respiration as monitored by a respiratory device, said respiratory device operative to output a respiratory signal indicative of the degree of a patient's respiration during a respiration cycle, said imaging device having a signal input for activating the imaging device in response to a preset signal, said system comprising:

a cycle processor, said cycle processor being externally coupled to said respiratory device operative to generate an electrical output signal that corresponds to said respiratory signal; and a generating device in communication with said cycle processor, said generating device outputting the preset signal to said imaging device in response to the electrical output signal received from said cycle processor.

11. The system of claim 10 wherein said cycle processor is optically coupled to the respiratory device.

12. The system as defined in claim 10 wherein said generating device comprises a solid state circuit.

13. The system as defined in claim 12 wherein said solid state circuit comprises a flip-flop having an input coupled to said respiratory signal from said respiratory device, said flip-flop having an output signal connected to a switch whereby said output signal causes said switch to change from a first state to a second state, said second state corresponding to said preset signal.

14. The invention as defined in claim 13 wherein said switch comprises a transistor.

* * * * *